United States Patent
Rafert et al.

[11] Patent Number: 5,817,008
[45] Date of Patent: Oct. 6, 1998

[54] CONFORMAL PULSE OXIMETRY SENSOR AND MONITOR

[75] Inventors: Stephen C. Rafert, Kent; David R. Marble, Seattle, both of Wash.; Glenn W. Pelikan, Portland, Oreg.; Alan Kahn, Minneapolis, Minn.

[73] Assignee: SpaceLabs Medical, Inc., Redmond, Wash.

[21] Appl. No.: 741,735

[22] Filed: Oct. 31, 1996

[51] Int. Cl.$^6$ ........................................ A61B 5/00
[52] U.S. Cl. ........................................ 600/323; 600/344
[58] Field of Search ........................ 128/633, 664, 128/665, 666; 356/41; 600/310, 322, 323, 340, 344, 473, 476

[56] References Cited

U.S. PATENT DOCUMENTS

| | | | |
|---|---|---|---|
| 2,706,927 | 4/1955 | Wood | 88/14 |
| 3,167,658 | 1/1965 | Richter | 250/239 |
| 3,170,459 | 2/1965 | Phipps et al. | 128/2.06 |
| 3,599,629 | 8/1971 | Gordy | 128/2.06 E |
| 3,602,213 | 8/1971 | Howell et al. | 128/2.05 F |
| 3,638,640 | 2/1972 | Shaw | 128/2 R |
| 3,698,382 | 10/1972 | Howell | 128/2 R |
| 3,704,706 | 12/1972 | Herczfeld et al. | 128/2 R |
| 3,769,974 | 11/1973 | Smart et al. | 128/2.05 P |
| 3,799,672 | 3/1974 | Vurek | 356/41 |
| 3,807,388 | 4/1974 | Orr et al. | 128/205 R |
| 3,847,483 | 11/1974 | Shaw et al. | 356/41 |
| 3,943,918 | 3/1976 | Lewis | 128/2.1 A |
| 3,980,075 | 9/1976 | Heule | 128/2.05 R |
| 3,998,550 | 12/1976 | Konishi et al. | 356/39 |
| 4,013,067 | 3/1977 | Kresse et al. | 128/2.05 R |
| 4,038,976 | 8/1977 | Hardy et al. | 128/2.05 P |
| 4,052,977 | 10/1977 | Kay | 128/2 V |
| 4,086,915 | 5/1978 | Kofsky et al. | 128/2 L |
| 4,091,803 | 5/1978 | Pinder | 128/2.05 P |
| 4,109,643 | 8/1978 | Bond et al. | 128/2 L |
| 4,121,573 | 10/1978 | Crovella et al. | 128/2.1 A |
| 4,167,331 | 9/1979 | Nielsen | 356/39 |
| 4,223,680 | 9/1980 | Jobsis | 128/633 |
| 4,266,554 | 5/1981 | Hamaguri | 128/633 |
| 4,281,645 | 8/1981 | Jöbsis | 128/633 |
| 4,305,401 | 12/1981 | Reissmueller et al. | 128/690 |
| 4,321,930 | 3/1982 | Jöbsis et al. | 128/633 |
| 4,350,165 | 9/1982 | Striese | 128/640 |
| 4,353,372 | 10/1982 | Ayer | 128/640 |
| 4,370,984 | 2/1983 | Cartmell | 128/640 |
| 4,380,240 | 4/1983 | Jöbsis et al. | 128/633 |
| 4,406,289 | 9/1983 | Wesseling et al. | 128/670 |
| 4,407,290 | 10/1983 | Wilber | 128/633 |
| 4,424,814 | 1/1984 | Secunda | 128/663 |

(List continued on next page.)

FOREIGN PATENT DOCUMENTS

| | | |
|---|---|---|
| 671279 | 10/1963 | Canada . |
| 0 019 478 | 11/1980 | European Pat. Off. . |
| 2 039 364 | 8/1980 | United Kingdom . |

*Primary Examiner*—Jennifer Bahr
*Assistant Examiner*—Eric F. Winakur
*Attorney, Agent, or Firm*—Seed and Berry LLP

[57] ABSTRACT

An optoelectronic pulse oximetry sensor is described which physically conforms to a body portion of a patient, such as a finger, and provides a firm pressing engagement between the sensor and the patient's body portion. The sensor includes a flexible substrate, such as an elastic bandage-type material, which is physically conformable and attachable/adherable to the patient's body portion. The sensor also includes a light source assembly for transilluminating the patient's body portion, and a light detector assembly for measuring transmitted light. The dimensions of the light source and light detector assemblies are constructed to provide a high aspect ratio relative to the flexible substrate. When the sensor is conformably applied to the patient's body portion, localized pressure is exerted on the body portion at the points of contact with the light source and light detector assemblies, thereby stressing the skin and the underlying blood-perfused tissue. The stress imparted to the skin and underlying tissues affects the distributions of blood in the tissues and provides improved accuracy and sensitivity in arterial oxygen saturation measurement, especially in circumstances of low perfusion.

40 Claims, 3 Drawing Sheets

U.S. PATENT DOCUMENTS

| | | | |
|---|---|---|---|
| 4,494,550 | 1/1985 | Blazek et al. | 128/664 |
| 4,510,938 | 4/1985 | Jöbsis et al. | 128/633 |
| 4,621,643 | 11/1986 | New, Jr. et al. | 128/633 |
| 4,653,498 | 3/1987 | New, Jr. et al. | 128/633 |
| 4,685,464 | 8/1987 | Goldberger et al. | 128/633 |
| 4,700,708 | 10/1987 | New, Jr. et al. | 128/633 |
| 4,726,382 | 2/1988 | Boehmer et al. | 128/667 |
| 4,759,369 | 7/1988 | Taylor | 128/633 |
| 4,770,179 | 9/1988 | New, Jr. et al. | 128/633 |
| 4,825,879 | 5/1989 | Tan et al. | 128/633 |
| 4,830,014 | 5/1989 | Goodman et al. | 128/665 |
| 4,859,057 | 8/1989 | Taylor et al. | 356/41 |
| 4,865,038 | 9/1989 | Rich et al. | 128/633 |
| 4,964,408 | 10/1990 | Hink et al. | 128/633 |
| 5,035,243 | 7/1991 | Muz | 128/633 |
| 5,041,187 | 8/1991 | Hink et al. | 156/634 |
| 5,069,213 | 12/1991 | Polczynski | 128/633 |
| 5,099,842 | 3/1992 | Mannheimer et al. | 128/633 |
| 5,237,994 | 8/1993 | Goldberger | 128/633 |
| 5,335,659 | 8/1994 | Pologe | 128/633 |
| 5,427,093 | 6/1995 | Ogawa et al. | 128/633 |

CONFORMAL PULSE OXIMETRY SENSOR AND MONITOR

TECHNICAL FIELD

The present invention relates generally to pulse oximetry instruments, and more particularly, to an optoelectronic pulse oximetry sensor which is physically conformable to a body portion of a patient.

BACKGROUND OF THE INVENTION

Oximeters are well known in the art, and are used to measure the level of oxygen in a patient's blood non-invasively. More precisely, oximeters measure the level of arterial oxygen saturation, which is the ratio of arterial blood oxyhemoglobin concentration to total hemoglobin concentration. Optoelectronic pulse oximeters are well known in the art and typically include a sensor having a light source, such as a light-emitting diode (LED), and a light sensor, such as a photodetector. The light source emits light which transilluminates—that is, shines through—the patient's body portion, and light which is neither absorbed nor scattered away by the blood-perfused tissue is measured by the light sensor.

Although broad-spectrum visual light may be employed, more typically light of two or more discrete wavelengths, such as red and infrared wavelengths, is used. The red light is primarily absorbed by the oxyhemoglobin, whereas the infrared light is primarily absorbed by all blood hemoglobin, independent of the oxyhemoglobin concentration. The absorption of the red and infrared light then varies as a function of the quantity of hemoglobin and the quantity of oxyhemoglobin in the lightpaths. Both the quantity of hemoglobin and the quantity of oxyhemoglobin vary as a function of the heartbeat cycle—namely, with the pulsatile distention of the arteries.

The amount of light received at the light sensor also depends on effects other than light absorption by blood hemoglobin, such as the effects due to bone, skin pigmentation, etc. However, these other effects do not vary as a function of the heartbeat cycle. Also, the light absorbing effects due to venous blood hemoglobin do not vary with the heartbeat cycle nearly as much as the effects due to arterial blood hemoglobin, since the capillary bed essentially isolates the veins from the high blood pressure pulse. Thus, the light received by the light sensor has both an alternating component (associated primarily with the arterial blood hemoglobin) and a steady-state component (associated with other light absorbing and/or scattering effects of the patient's body portion). As is well known in the art, determining the ratios of the alternating components to the steady-state components allows an accurate determination of arterial oxygen saturation, independent of the light absorbing and/or scattering effects associated with the steady-state component.

Typically, the amplitude of the alternating component is of the order of 2%–3% of the total light received by the light sensor. In circumstances of low perfusion, such as when the patient's body portion is particularly cold, or when a patient is in shock, experiencing declining blood pressure, etc., the amplitude of the alternating component can be of the order of only 1% of the total light received by the light sensor. Thus, any signal noise and/or other spurious effecting tending to mimic the alternating component can detrimentally affect measurement accuracy. Accordingly, currently available oximeters include hardware circuitry and a variety of signal processing software algorithms for performing noise reduction and other signal processing.

The effect of a patient's blood oxygen content on the intensity of transmitted light is well known, and is described in U.S. Pat. Nos. 4,621,643, 4,653,498, 4,685,464, and 4,700,708, which are incorporated herein by reference. Also well known in the art are pulse oximetry sensors that are placed on the patient's body portion and substantially physically conformed to that body portion. One example is U.S. Pat. No. 4,830,014 to Goodman et al., incorporated herein by reference. The sensor described in Goodman et al. includes an elongated flexible strip (much like an elastic bandage) to which an LED and a photodetector are attached. The LED and photodetector have a very small physical profile. The LED and photodetector are essentially integrated within the flexible strip so that they do not stress the skin by imparting localized pressure to the skin beneath the LED and light detector. The sensor described in Goodman et al. readily conforms to the body portion, such as a finger, on which it is placed or wrapped.

The sensor described in Goodman et al. exhibits a number of disadvantages. In particular, the sensor would not work well unless firmly applied to the patient, and even then would provide a measured pulse amplitude which may be insufficient for accurate measurement of a patient's pulse and blood oxygen level. In particular, the primary goal taught by Goodman et al., i.e., avoiding the application of localized stress to the skin (and hence stress, to blood-perfused tissue beneath the skin), actually impairs the ability of the sensor to provide accurate blood oxygen levels.

SUMMARY OF THE INVENTION

In accordance with the present invention, an improved optoelectronic pulse oximetry sensor is provided which substantially physically conforms to a body portion of a patient. The sensor is removably securable to the patient's body portion by an adhesive coating, and includes at least one light source for transilluminating the body portion and a light detector for measuring light transmitted through the body portion. The sensor includes a flexible substrate having an inner surface and an outer surface—the inner surface disposed towards the body portion and the outer surface disposed away from the body portion. The light source and the light detector are mounted on the flexible substrate at spaced-apart locations. Significantly, the light source and the light detector project a substantial distance from the inner surface to provide firm localized pressure against the body portion, thereby stressing blood-perfused tissues beneath the skin.

In one embodiment, the light source and light detector are each enclosed in a substantially rigid transparent housing. Each of the housings includes a flange portion securable between an inner layer and an outer layer forming the flexible substrate. In another embodiment, each of the light source and light detector includes a substantially rigid circuit board for holding a light source or a light detector and providing electrical connections thereto. A substantially elastomeric transparent cover is connected to the circuit board and covers the corresponding light source or light detector.

DETAILED DESCRIPTION OF THE INVENTION

An improved pulse oximetry sensor is described which substantially physically conforms to a body portion of a patient, such as a finger, while providing sufficient stress to the patient's body portion to afford greater accuracy of measurement. In the following description, certain specific details are set forth in order to provide a thorough understanding of the preferred embodiment of the present invention. However, it will be obvious, to one skilled in the art, that the present invention may be practiced without these details. In other instances, well-known pulse oximetry sensor components are not discussed in detail in order not to unnecessarily obscure the invention.

Figure 1:
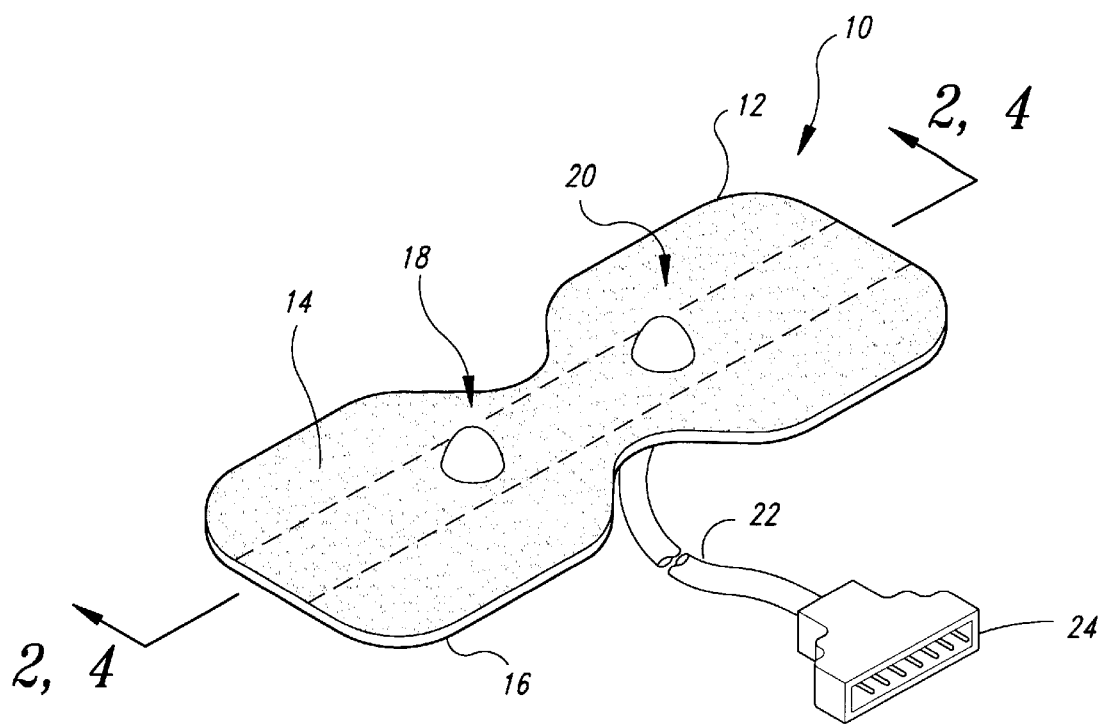
FIG. 1 is an isometric view of an optoelectronic pulse oximetry sensor having a flexible substrate, a light source assembly, and a light detector assembly according to the present invention.

FIG. 1 shows a preferred embodiment of an optoelectronic pulse oximetry sensor 10 made in accordance with the present invention. The sensor 10 includes a flexible substrate 12, such as an elastic bandage-type material. The flexible substrate 12 is preferably constructed from a plurality of layers which are bonded or otherwise connected to one another. The flexible substrate 12 includes an inner surface 14 and an outer surface 16. The designations of "inner" and "outer" correspond with the intended orientation of the flexible substrate 12 upon physical conformation with the patient's body portion. The flexible substrate 12 preferably includes a conventional adhesive on the inner surface 14 to securely attach and conform the sensor 10 to the patient's body portion. Alternatively, if the ends of the substrate 12 overlap, a hook-and-loop type fastener of the type commonly sold under the trademark Velcro® may be suitably employed.

A light source assembly 18 and a light detector assembly 20 are attached to the flexible substrate 12. The dimensions of the light source assembly 18 and light detector assembly 20 are constructed to provide a high aspect ratio relative to the flexible substrate 12. In this way, the light source and light detector assemblies 18, 20 project a substantial distance from the inner surface 14 of the flexible substrate 12. When the inner surface of the flexible substrate 12 is placed against the skin of the patient's body portion, the light source and detector assemblies 18, 20 firmly press into the skin to apply substantial stress to the skin and the blood-perfused tissue beneath the skin. Consequently, the skin and the underlying tissue are displaced and deformed, thereby partially depleting the tissue of blood. As shown in the embodiments depicted in FIGS. 2 and 4, the source and detector assemblies 18, 20 project from the flexible substrate 12 a distance that is not less than approximately the distance they extend along the substrate—i.e., having an aspect ratio relative to the flexible substrate of not less than approximately 1:1.

As in conventional pulse oximetry sensors, the light source assembly 18 may include two light-emitting diodes (LEDs) emitting light at red and infrared wavelengths, and the light detector assembly 20 may include a corresponding two or more photodetectors, although a single light detector is normally used to detect light at both wavelengths. Electric signals are carried to and from the light source and light detector assemblies 18, 20 by a multistrand electric cable 22, which terminates at an electrical connector 24 to which conventional optoelectronic oximeter control and processing circuitry is attached.

The high aspect ratio of the light source and light detector assemblies 18, 20 provides a number of distinct advantages over prior art pulse oximetry sensors. Some conventional pulse oximetry sensors, including sensors like that described in Goodman et al., do not apply pressure to the patient's body portion at the points of contact with the light source and/or light detector to achieve optimum performance. As mentioned above, when the sensor 10 is placed in substantial physical conformance with the patient's body portion, the light source and light detector assemblies 18, 20 each project a substantial distance from the inner surface 14 of the flexible substrate 12 into firm pressing engagement with the patient's body portion.

By exerting pressure at the points of contact, localized stress is imparted to blood-perfused tissue beneath the light source and detector assemblies 18, 20. This localized stress forces some of the blood from the blood-perfused tissues adjoining the points of contact. Because a patient's arterial blood is at a higher pressure than the venous blood, a greater quantity of venous blood will be removed. This removal of venous blood correspondingly decreases associated light attenuation effects and thereby increases the amount of light reaching the light detector assembly 20, from which the measurements of arterial blood oxygen saturation levels are determined. Also, because the venous blood has been largely depleted from the transilluminated body portion, any localized pulse effects in the veins (due to pulsatile distention of adjacent arteries) is minimized. This is particularly advantageous since arterial oxygen saturation is of primary clinical interest. When the patient's heart beats, there is a momentary increase in the arterial pressure and a corresponding increase in arterial blood quantity, thereby causing a momentary decrease in the amount of light received at the light detector assembly 20, from which the patient's pulse is determined.

The localized pressure exerted by the light source and detector assemblies 18, 20 partially depletes the tissue portions adjacent to the assemblies of blood. These tissue portions then become more and less depleted of blood as a function of the heartbeat cycle, thereby enhancing the alternating component of the light received at the light detector assembly 20. Also, a boundary region separating the blood-depleted tissue portions from the surrounding blood-perfused tissue portions changes position as a function of the heartbeat cycle and creates a shutter-like effect, which further enhances the alternating component of the light received at the light detector assembly 20. The enhanced amplitude of the alternating component provided by the sensor 10 affords improved reliability, accuracy, and sensitivity in arterial oxygen saturation measurement. This is especially advantageous when arteries are constricted, as when dealing with low perfusion states.

Figure 2:
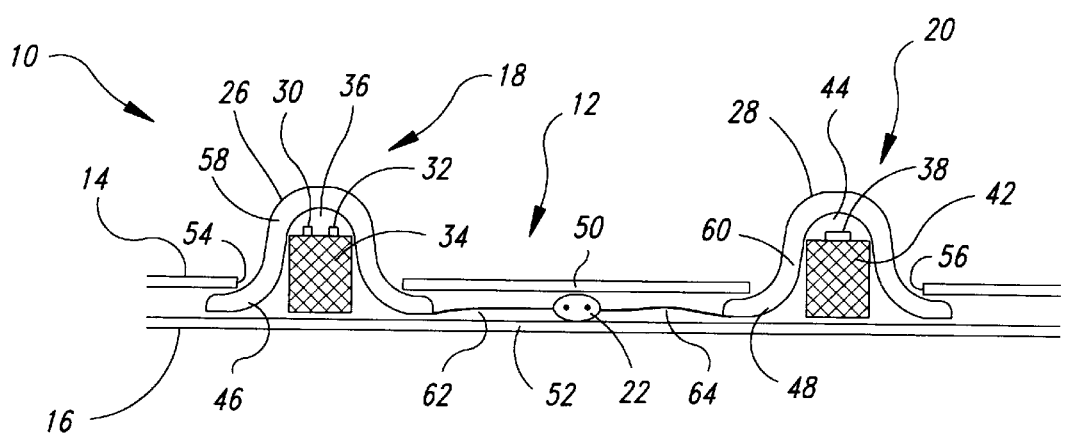
FIG. 2 is an enlarged cross-sectional view of the sensor of FIG. 1, showing certain details of a preferred embodiment of the light source and light detector assemblies.

FIG. 2 shows a cross-section of the sensor 10 of FIG. 1, and depicts a preferred embodiment of the light source and light detector assemblies 18, 20. Each of the light source and light detector assemblies 18, 20 includes a rigid transparent housing 26, 28, respectively, enclosing other components of the light source and light detector assemblies. The transparent housings 26, 28 then provide the firm pressing engagement between the light source and light detector assemblies 18, 20 and the patient's body portion. The light source assembly 18 includes a plurality of light sources, such as a red LED 30 and an infrared LED 32. The LEDs 30, 32 are mounted on a substantially rigid LED holder 34, which preferably includes a printed circuit board for making the appropriate electrical connections. The LEDs 30, 32 may be encased by a protective covering material 36, such as silicone, although the transparent housing 26 itself can provide sufficient protection. The light detector assembly 20 includes a single photodetector 38 operable to detect light received from the red LED 30 and the infrared LED 32. The photodetector 38 is mounted on a substantially rigid photodetector holder 42, which preferably includes a printed circuit board for making the appropriate electrical connections. The photodetector 38 may be encased by protective covering 44, such as silicone, although the transparent housing 28 itself can provide sufficient protection.

Each of the transparent housings 26, 28 includes a flange portion 46, 48, respectively, which extends between an inner layer 50 and an outer layer 52 of the flexible substrate 12. The flange portions 46, 48 are held between the inner and outer layers 50, 52 to secure the light source and light detector assemblies 18, 20 to the flexible substrate 12. The inner layer 50 includes first and second openings 54, 56 through which a cover portion 58, 60 of the transparent housings 26, 28 extend, all respectively. The cover portions 58, 60 are preferably rounded so as to minimize any shearing effects when applied to a patient's skin. This shape also provides a smooth boundary transition from the blood-depleted tissue portions to the surrounding blood-perfused tissue portions, which enhances the mobility of the boundary region in response to the heartbeat cycle. Correspondingly, this enhances the amplitude of the alternating component of the light received at the light detector assembly 20. Also held between the inner and outer layers 50, 52 are the various electric wires 62, 64 connecting to the light source and light detector assemblies 18, 20, respectively. The electric wires 62, 64 are gathered together at the multistrand electric cable 22, which then emerges from the flexible substrate 12 at a position approximately midway between the light source and light detector assemblies 18, 20 (see also FIG. 1).

Figure 3:
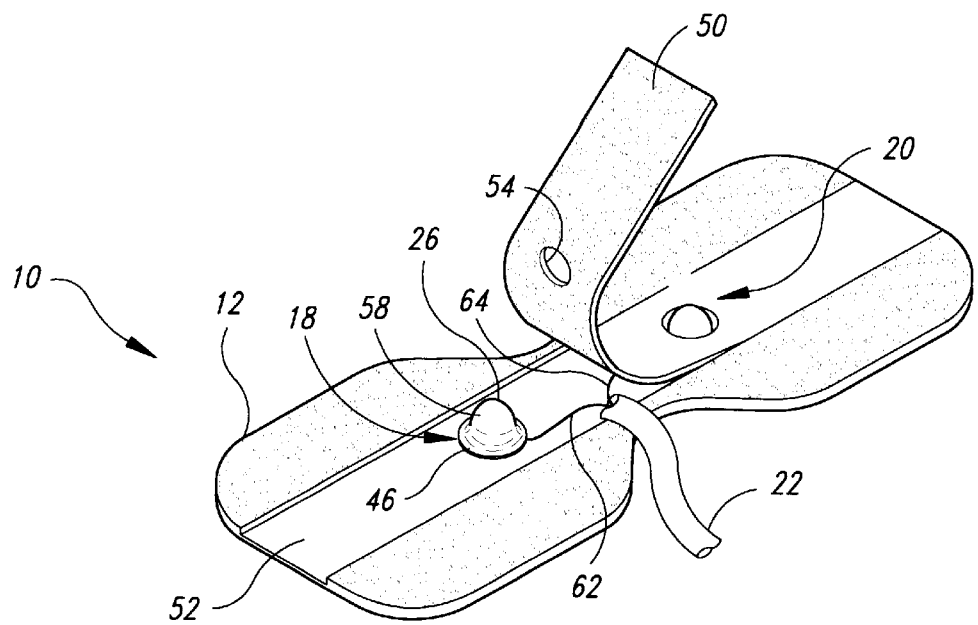
FIG. 3 is an isometric view of the sensor of FIG. 1, having the light source and light detector assemblies of FIG. 2, showing a portion of the flexible substrate pulled back to expose certain details of the inner construction.

FIG. 3 shows a portion of the inner layer 50 pulled away to show how the light source and light detector assemblies 18, 20 are secured to the flexible substrate 12. In particular, the opening 54 in the inner layer 50 is placed over the cover portion 58 of the transparent housing 26 of the light source assembly 18. The inner and outer layers 50, 52, when bonded or otherwise attached, then hold in place the transparent housing 26 by virtue of the flange portion 46 held securely therebetween. Also shown is the routing of electric wires 62, 64 and the electric cable 22.

Figure 4:
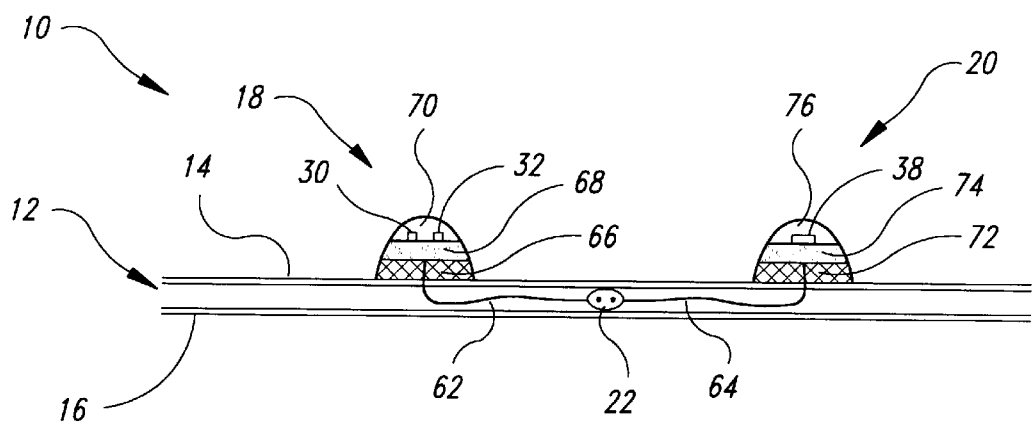
FIG. 4 is an enlarged cross-sectional view of the sensor of FIG. 1, showing an alternate embodiment of the light source and light detector assemblies.

FIG. 4 is a cross-sectional view like that of FIG. 2, but showing an alternate embodiment of the light source and light detector assemblies 18, 20. In this alternate embodiment, the flexible substrate 12 may be suitably constructed from a single layer, or from two layers carrying the electric wires 62, 64 and a portion of the electric cable 22 therebetween. If the flexible substrate 12 is of a single layer construction, the electric wires 62, 64 would preferably pass through the flexible substrate 12 and be gathered together at the electric cable 22 proximate to (or attached to) the outer surface 16 of the flexible substrate 12.

The light source assembly 18 includes a flexible support pad 66, such as a soft foam pad, which is bonded by glue or other suitable means to the inner surface 14 of the flexible substrate 12. A substantially rigid LED holder, such as a printed circuit board 68, is mounted on the support pad 66. The printed circuit board 68 provides the appropriate electrical connections between the electric wires 62 and the LEDs 30, 32 which are mounted on the printed circuit board. The electric wires 62 preferably pass from the printed circuit board 68 through the flexible support pad 66. The LEDs 30, 32 are mounted on the printed circuit board 68 and enclosed by a rounded soft protective cover, such as a silicone cap 70. When the sensor 10 is placed in physical conformance with the patient's body portion, the silicone cap 70 is pressed into firm engagement with the patient's body portion to exert localized pressure thereon. This localized pressure stresses the skin, and hence the underlying blood-perfused tissues, and the consequent compression of the skin and underlying tissue partially depletes the underlying tissue of blood.

The light detector assembly 20 is similarly constructed. A flexible support pad 72, such as a soft foam pad, is attached to the inner surface 14 of the flexible substrate 12. The electric wires 64 pass through the support pad 72 and connect to a substantially rigid photodetector holder, such as a printed circuit board 74. The printed circuit board 74 provides the appropriate electrical connections to the photodetector 38 which is mounted on the printed circuit board. The photodetector 38 is enclosed by a rounded protective cover, such as a silicone cap 76, which exerts localized pressure on the patient's body portion when the sensor 10 is placed in physical conformance therewith.

Figure 5:
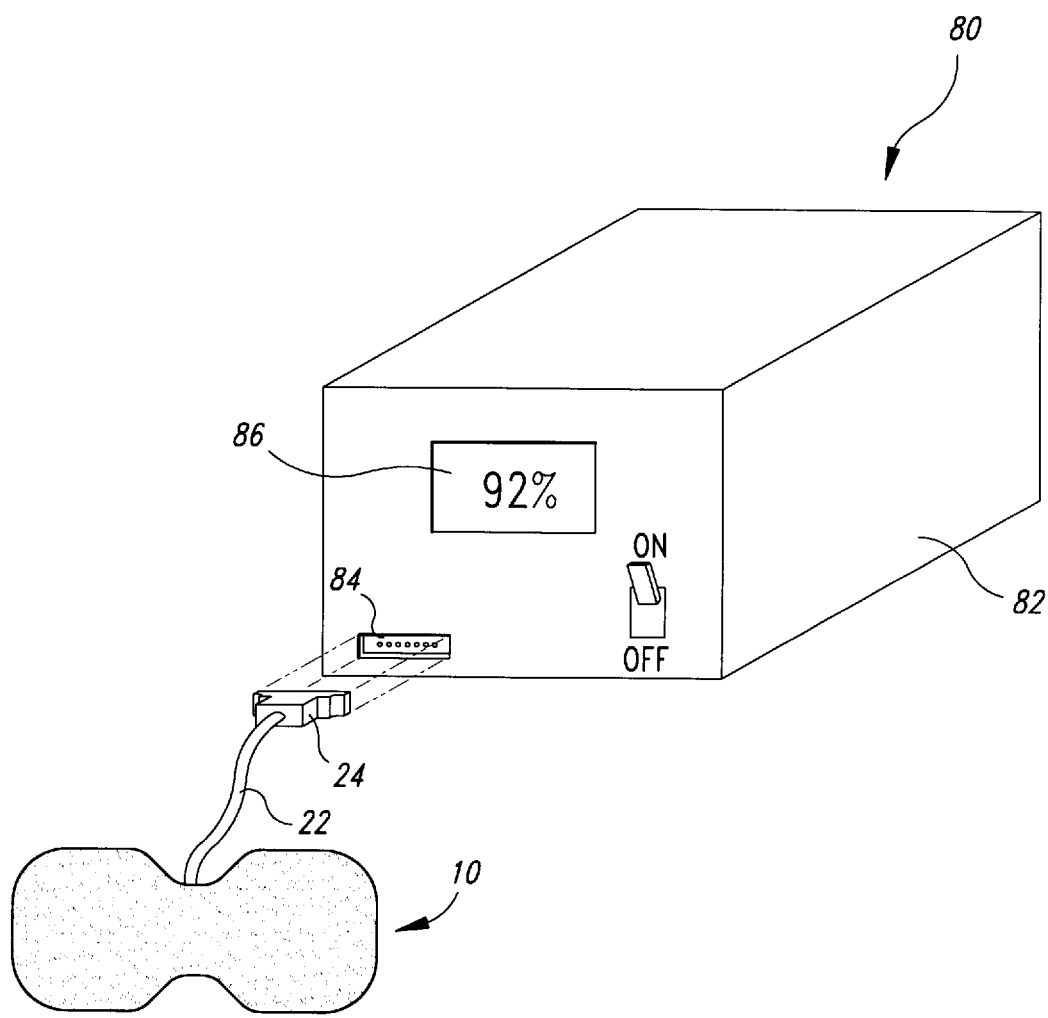
FIG. 5 is an isometric view showing the sensor of FIG. 1 connected to a conventional pulse oximetry monitor.

The sensor 10 of FIG. 1 is shown in FIG. 5 connected to a conventional pulse oximetry monitor 80. As is well known in the art, the monitor 80 is housed in a case 82 and has conventional internal circuitry (not shown) to provide appropriate drive signals to the LEDs 30, 32 (see FIGS. 2 and 4) through a connector 84. The case 82 also houses conventional circuitry (not shown) for receiving the output signal of the photodetector 38 (see FIGS. 2 and 4) via the connector 84 and for determining the percentage of oxygen saturation in blood-perfused tissues in a body part to which the sensor 10 is attached. The circuitry then displays the oxygen saturation percent in a display window 86 in a conventional manner.

It will be appreciated that, although the various embodiments of the invention have been described above for purposes of illustration, a number of modifications may be made without deviating from the spirit and scope of the invention. For example, the light source and light detector assemblies 18, 20 may be constructed in any of a wide variety of ways and in a variety of shapes, but all having a high aspect ratio relative to the flexible substrate 12 sufficient to provide the attendant localized pressure on a patient's body portion to achieve the advantages described above. Those skilled in the art will understand that the advantages described above may be obtained by adapting only one of the light source and light detector assemblies 18, 20 to provide the requisite localized pressure on the patient's body portion. Additionally, any of a wide variety of suitable means may be employed for attaching and/or adhering the flexible substrate 12 to the patient's body portion. Similarly, any of a wide variety of means for securing the light source and light detector assemblies 18, 20 to the flexible substrate 12 may be employed. Indeed, numerous variations are well within the scope of this invention. Accordingly, the invention is not limited except as by the appended claims.

We claim:

1. An optoelectronic sensor removably securable to a body portion of a patient, comprising:

an elastic substrate having an inner surface for disposition towards the body portion and an outer surface for disposition away from the body portion;

a light source assembly mounted on the elastic substrate; and a light detector assembly mounted on the elastic substrate;

wherein at least one of the light source and light detector assemblies projects away from the inner surface of the elastic substrate, and wherein the elastic substrate is adapted to press the one of the light source and light detector assemblies into firm pressing engagement with the body portion to exert a localized pressure thereon.

2. The sensor of claim 1 wherein the light source assembly comprises a light source and a substantially rigid transparent housing enclosing the light source.

3. The sensor of claim 2 wherein the substrate comprises inner and outer substrate layers, and wherein the transparent housing comprises a hollow body portion having a transparent cover portion at one end and a flange at the other end, the flange being positioned between the inner and outer substrate layers with the cover portion projecting through a hole in the inner substrate layer.

4. The sensor of claim 1 wherein the light detector assembly comprises a light detector and a substantially rigid transparent housing enclosing the light detector.

5. The sensor of claim 4 wherein the substrate comprises inner and outer substrate layers, and wherein the transparent housing comprises a hollow body portion having a transparent cover portion at one end and a flange at the other end, the flange being positioned between the inner and outer substrate layers with the cover portion projecting through a hole in the inner substrate layer.

6. The sensor of claim 1 wherein the light source assembly comprises:

a light source;

a substantially rigid circuit board for holding the light source and providing electrical connections thereto; and a substantially elastomeric transparent cover connected to the circuit board and covering the light source.

7. The sensor of claim 6 wherein the light source assembly further includes an elastomeric layer attached to the flexible substrate on a first side and attached to the circuit board on a second side.

8. The sensor of claim 1 wherein the light detector assembly comprises:

a light detector;

a substantially rigid circuit board for holding the light detector and providing electrical connections thereto; and a substantially elastomeric transparent cover connected to the circuit board and covering the light detector.

9. The sensor of claim 8 wherein the light detector assembly further includes an elastomeric layer attached to the elastic substrate on a first side and attached to the circuit board on a second side.

10. The sensor of claim 1 wherein the elastic substrate includes:

an outer layer providing the outer surface;

an inner layer attached to the outer layer and providing the inner surface, the inner layer having an opening; and wherein the light source assembly is attached to the elastic substrate at a location between the inner and outer layers and extends through the opening in the inner layer.

11. The sensor of claim 10 wherein the light source assembly includes a substantially rigid transparent housing enclosing the light source and having a flange portion and a cover portion, the flange portion being held between the outer and inner layers to attach the light source assembly to the elastic substrate, and the cover portion projecting through the opening in the inner layer.

12. The sensor of claim 10 wherein a plurality of electric wires carrying electric signals to and from the light source and light detector assemblies are partly held between the outer and inner layers.

13. An optoelectronic sensor removably securable to a body portion of a patient and having a light source for transilluminating the body portion and a light detector for measuring transmitted light, the sensor comprising:

a flexible substrate having an inner surface for disposition towards the body portion and an outer surface for disposition away from the body portion, the flexible substrate providing a substantially uniform pressure on the body portion;

a light source assembly connected to the flexible substrate and projecting from the inner surface a distance that is not less than approximately a distance that the light source assembly extends along the inner surface, the light source assembly thereby adapted to exert a first localized pressure against the body portion beneath the light source assembly to stress skin beneath the light source assembly; and a light detector assembly connected to the flexible substrate and projecting from the inner surface a distance that is not less than approximately a distance that the light detector assembly extends along the inner surface, the light detector assembly thereby adapted to exert a second localized pressure against the body portion beneath the light detector assembly to stress skin beneath the light detector assembly.

14. The sensor of claim 13 wherein the flexible substrate includes a plurality of layers.

15. The sensor of claim 13 wherein the first and second localized pressures are approximately equal.

16. An optoelectronic sensor removably securable to a body portion of a patient and having a light source for transilluminating the body portion and a light detector for measuring transmitted light, the sensor comprising:

a flexible substrate physically conformable to the body portion and including an outer layer and an inner layer, the inner layer attached to the outer layer and having a first opening and a second opening;

a light source assembly including a first substantially rigid transparent housing enclosing the light source and having a first flange portion and a first cover portion, the flange portion being positioned between the outer and inner layers to secure the light source assembly to the flexible substrate, the first cover portion projecting through the first opening in the inner layer and having an aspect ratio relative to the flexible substrate of not less than approximately 1:1, the light source assembly thereby adapted to exert a localized pressure against the body portion beneath the light source assembly to stress skin beneath the light source assembly; and a light detector assembly including a second substantially rigid transparent housing enclosing the light detector and having a second flange portion and a second cover portion, the second flange portion being positioned between the outer and inner layers to secure the light detector assembly to the flexible substrate, the second cover portion projecting through the second opening in the inner layer and having an aspect ratio relative to the flexible substrate of not less than approximately 1:1, the light detector assembly thereby adapted to exert a localized pressure against the body portion beneath the light detector assembly to stress skin beneath the light detector assembly.

17. The sensor of claim 16 wherein the light source assembly includes a plurality of light-emitting diodes.

18. A pulse oximetry monitoring system, comprising:
an optoelectronic sensor removably securable to a body portion of a patient, comprising:
a flexible substrate having an inner surface for disposition towards, the body portion and an outer surface for disposition away from the body portion;
a light source assembly mounted on the flexible substrate, the light source assembly projecting away from the inner surface a distance that is not less than approximately a distance the light source assembly extends along the inner surface, the light source assembly thereby adapted to exert localized pressure on the body portion beneath the light source assembly when the sensor is attached to the body portion; and
a light detector assembly mounted on the flexible substrate, the light detector assembly projecting away from the inner surface a distance that is not less than approximately a distance the light detector assembly extends along the inner surface, the light detector assembly thereby adapted to exert localized pressure on the body portion beneath the light detector assembly when the sensor is attached to the body portion; and
a pulse oximetry monitor electrically coupled to the optoelectronic sensor, the monitor applying a drive signal to the light source assembly, receiving a signal from the light detector assembly, and determining the percentage of oxygen saturation of blood in tissue in the body portion of the patient between the light emitter assembly and the light detector assembly.

19. The pulse oximetry monitoring system of claim 18 wherein the light source assembly comprises a light source and a substantially rigid transparent housing enclosing the light source.

20. The pulse oximetry monitoring system of claim 19 wherein the substrate comprises inner and outer substrate layers, and wherein the transparent housing comprises a hollow body portion having a transparent cover portion at one end and a flange at the other end, the flange being positioned between the inner and outer substrate layers with the cover portion projecting through a hole in the inner substrate layer.

21. The pulse oximetry monitoring system of claim 18 wherein the light detector assembly comprises a light detector and a substantially rigid transparent housing enclosing the light detector.

22. The pulse oximetry monitoring system of claim 21 wherein the substrate comprises inner and outer substrate layers, and wherein the transparent housing comprises a hollow body portion having a transparent cover portion at one end and a flange at the other end, the flange being positioned between the inner and outer substrate layers with the cover portion projecting through a hole in the inner substrate layer.

23. The pulse oximetry monitoring system of claim 18 wherein the light source assembly comprises:
a light source;
a substantially rigid circuit board for holding the light source and providing electrical connections thereto; and
a substantially elastomeric transparent cover connected to the circuit board and covering the light source.

24. The pulse oximetry monitoring system of claim 23 wherein the light source assembly further includes an elastomeric layer attached to the flexible substrate on a first side and attached to the circuit board on a second side.

25. The pulse oximetry monitoring system of claim 18 wherein the light detector assembly comprises:
a light detector;
a substantially rigid circuit board for holding the light detector and providing electrical connections thereto; and
a substantially elastomeric transparent cover connected to the circuit board and covering the light detector.

26. The pulse oximetry monitoring system of claim 25 wherein the light detector assembly further includes an elastomeric layer attached to the flexible substrate on a first side and attached to the circuit board on a second side.

27. The pulse oximetry monitoring system of claim 18 wherein the flexible substrate includes:
an outer layer providing the outer surface;
an inner layer attached to the outer layer and providing the inner surface, the inner layer having an opening; and
wherein the light source assembly is attached to the flexible substrate at a location between the inner and outer layers and extends through the opening in the inner layer.

28. The pulse oximetry monitoring system of claim 24 wherein the light source assembly includes a substantially rigid transparent housing enclosing the light source and having a flange portion and a cover portion, the flange portion being held between the outer and inner layers to attach the light source assembly to the flexible substrate, and the cover portion projecting through the opening in the inner layer.

29. The pulse oximetry monitoring system of claim 27 wherein a plurality of electric wires carrying electric signals to and from the light source and light detector assemblies are partly held between the outer and inner layers.

30. A method of measuring the arterial oxygen saturation level in a patient, comprising the steps of:
physically conforming an arterial oxygen saturation level sensor to a body portion of the patient;
directing light into the body portion at a light source region of the body portion;
detecting light transmitted through the body portion at a light detection region of the body portion; and
exerting a localized pressure at one of the light source and light detection regions to stress blood-perfused tissue and partially remove blood from the one of the regions.

31. A method according to claim 30 wherein the step of exerting a localized pressure includes creating a boundary region separating blood-depleted portions of the one of the regions from surrounding blood-perfused portions.

32. A method according to claim 31, further comprising the step of sensing movement of the boundary region.

33. A method of measuring the arterial oxygen saturation level in a patient, comprising the steps of:
physically conforming an arterial oxygen saturation level sensor to a body portion of the patient;
directing light into the body portion at a light source region of the body portion;
detecting light transmitted through the body portion at a light detection region of the body portion;
partially depleting one of the light source and light detection regions of blood and creating a boundary region separating blood-depleted portions of the one of the regions from surrounding blood-perfused portions; and sensing movement of the boundary region.

34. A method according to claim 33 wherein the step of partially depleting one of the light source and light detection regions of blood includes the step of substantially removing venous blood from the one of the regions.

35. A method according to claim 33 wherein the step of partially depleting one of the light source and light detection regions of blood includes the step of partially removing arterial blood from the one of the regions.

36. A method according to claim 33 wherein the step of partially depleting one of the light source and light detection regions of blood includes the step of exerting a localized pressure on the one of the regions.

37. A method of measuring the arterial oxygen saturation level in a patient, comprising the steps of:

physically conforming an arterial oxygen saturation level sensor to a body portion of the patient;

directing light into the body portion at a light source region of the body portion;

detecting light transmitted through the body portion at a light detection region of the body portion;

substantially eliminating venous pulse effects in one of the light source and light detection regions; and sensing arterial pulse effects in the one of the regions.

38. A method according to claim 37 wherein the step of substantially eliminating venous pulse effects includes the step of substantially removing venous blood from the one of the regions.

le;2q39. A method according to claim 37 wherein the step of substantially eliminating venous pulse effects includes the step of exerting a localized pressure at the one of the regions.

40. A method according to claim 37 wherein the step of sensing arterial pulse effects includes the steps of:

forming a boundary region separating substantially blood-depleted portions from surrounding substantially blood-perfused portions of the one of the regions; and sensing movement of the boundary region.

* * * * *